United States Patent [19]

Pardini

[11] Patent Number: 4,708,870

[45] Date of Patent: Nov. 24, 1987

[54] METHOD FOR IMPARTING ANTIMICROBIAL ACTIVITY FROM ACRYLICS

[75] Inventor: Steven P. Pardini, Columbia, S.C.

[73] Assignee: E. I. Du Pont de Nemours and Company, Wilmington, Del.

[21] Appl. No.: 740,896

[22] Filed: Jun. 3, 1985

[51] Int. Cl.$^4$ .................. A61K 31/78; A61K 31/74; A61B 17/04; A61L 17/00

[52] U.S. Cl. .................. 424/81; 128/334 R; 128/335.5; 424/78; 514/953; 523/100; 523/105; 523/122; 526/329.3

[58] Field of Search .................. 424/78, 81; 526/329.3; 523/100, 105, 122; 514/953; 128/334 R, 335.5

[56] References Cited

U.S. PATENT DOCUMENTS

| | | | |
|---|---|---|---|
| 2,985,634 | 5/1961 | Schmidt et al. | 526/329.3 |
| 3,012,998 | 12/1961 | Wishman et al. | 526/329.3 |
| 3,197,430 | 7/1965 | Lowes . | |
| 3,223,547 | 12/1965 | Bindler et al. | 523/122 |
| 3,306,955 | 2/1967 | Lowes | 128/335.5 |
| 3,310,607 | 3/1967 | Lowes . | |
| 3,642,003 | 2/1972 | Kurtz | 128/335.5 |
| 3,896,813 | 7/1975 | Kurtz | 128/335.5 |
| 4,024,871 | 5/1977 | Stephenson | 128/335.5 |
| 4,049,605 | 9/1977 | Kobashi et al. | 526/329.3 |
| 4,062,857 | 12/1977 | Kobashi et al. | 526/329.3 |
| 4,259,103 | 3/1981 | Malek et al. . | |
| 4,383,053 | 5/1983 | Honda | 523/122 |
| 4,496,363 | 1/1985 | DeFilippi . | |

FOREIGN PATENT DOCUMENTS 3214610 11/1982 Fed. Rep. of Germany .
2342740 9/1977 France .

OTHER PUBLICATIONS

V. Konsulov, L. Konsulova, V. Baranovskii—Polyacrylates II. Synthesis and Studies of Copolymers of Methyl Methacrylate with Quaternary Salts of N,N-Dimethylaminoethyl Methacrylate, Khim. Ind. 56(1) 14-16 (Bulg.) 1984.
Konsulov, V. B., E. B. Monakhova, N. V. Shvets, V. V. Aver'yabova, L. A. Vol'f, in: New Developments in Organization, Engineering, and Technology of Textile and Light Industry [in Russian], Leningrad, 1976, p. 85.
Konsulov, V. B., N. V. Shvets, L. V. Emets, L. A. Vol'f, M. A. Korshunov, in: New Developments in Organization, Engineering, and Technology of Textile and Light Industry [in Russian], Leningrad, 1976, p. 90.

Primary Examiner—Ronald W. Griffin

[57] ABSTRACT

A method for imparting non-fugitive antimicrobial activity to an article of manufacture is disclosed which comprises forming the articles of manufacture from an acrylonitrile composition which includes up to 10% of a protonated amine. The antimicrobial activity is inherent in the acrylonitrile composition.

23 Claims, No Drawings

METHOD FOR IMPARTING ANTIMICROBIAL ACTIVITY FROM ACRYLICS

DESCRIPTION

1. Technical Field

This application relates to a method for imparting non-fugitive antimicrobial activity to an article of manufacture by forming the article from acrylic polymer fibers or fabrics.

2. Background

It is known that antimicrobial chemical agents can be spun into or topically applied to synthetic fibers. However, topical treatments are readily subjected to surface abrasion and eventually removed from the fiber. Additives are fugitive and after a limited number of wash and wear cycles the chemical agent can be depleted and the antimicrobial protection lost. A key uncertainty in these approaches is the additive level. The amount of additive needed to provide desired end use properties will depend upon the lifetime of the final product, the degree of blending with other fibers, the frequency of wash-and-wear cycles and the degree of abrasion during normal usage. The combination of these factors could require excessive additive levels which become prohibitive both economically and technically.

The main problem with the spun in approach is the toxicity of the additive. In certain end uses such as children's garments, medical products and intimate apparel, fugitive additives could have potentially toxic effects. Also, many synthetic fiber processes require elevated temperatures for extended periods of time or make use of exotic solvents under heat and pressure which could lead to unwanted side reactions of the additives that produce toxic by-products (e.g. dioxins), corrosive species (e.g., chlorides) and/or eliminate the additive's antimicrobial activity. This would result in production, handling and disposal problems and would require additional technologies to safely produce the fiber.

Surface-bonded, alkoxysilane quaternary-ammonium chlorides provide antimicrobial fiber protection. The bioactive quaternary-ammonium alkoxysilane is applied onto the fiber or final product from a methanol finish solution, and bonded to the surface by hydrolysis and condensation of the alkoxysilane with hydroxyl groups of the fiber. But in the case of acrylic, polyester, nylon and other fibers which are made of polymers that do not contain significant amounts of hydroxyl groups, the alkoxylsilanes cannot be bonded to the fiber surface by the hydrolysis and subsequent condensation reactions. Thus the siloxane would be merely a topical treatment to these fibers. Several problems have been encountered in this approach. The surface-applied finish has fugitive chloride counter ion which can easily exchange with organic phosphates and sulfonates; thus when the product is laundered the antimicrobial efficacy of the surface applied finish can be greatly reduced. Another significant problem is methanol release during the alkoxysilane bonding process, which can pose toxicity and potential flammability concerns. Finally, methoxysilyl compounds are incompatible with most aqueous, emulsion-based, textile finishes, which leads to undesirable, finish-application and durability problems.

SUMMARY OF THE INVENTION

It has now been discovered that certain types of acrylic polymers, fibers and fabrics have non-fugitive antimicrobial properties. In the present invention it was discovered that non-fugitive antimicrobial activity is imparted to acrylic polymers, fibers or fabrics made thereof, by copolymerization of an acrylic protonated amine comonomer and/or by use of protonated amine end groups.

The protonated amine sites are part of the acrylic polymer chain and thus their durability in the final product is independent of end use properties, such as lifetime of the final product, wash-and-wear cycle frequency and degree of abrasion during normal usage. Furthermore, diffusible, toxic additives which may pose serious concern in certain end uses are not present. Since the antimicrobial agent is part of the polymer itself, toxic byproducts from spinning and fiber processing conditions do not occur.

In addition, the protonated amines are distributed throughout the polymer and thus are present in all parts of the fiber and its surface. The equilibrium distribution of protonated amines is an inherent part of the fiber. The finding of antimicrobial activity of the fiber itself is surprising in light of the fact, as set out in U.S. Pat. No. 3,197,430, that fibers produced from acrylonitrile polymers were thought not to have the inherent ability to inhibit the growth of bacteria. The fiber of this invention is quite stable especially relative to the surface bound alkoxysilane quaternary amines which are readily deactivated by soap solutions.

An essential prerequisite to antimicrobial action is effective contact between the chemical agent and the microorganism. Upon effective contact, the chemical agent interacts with some critical component of the microbial structure and/or metabolism. Specific modes of action of antimicrobial compounds are difficult to determine and are complicated by concentration, pH, temperature, solvent, electrolyte and phase separation effects.

The term antimicrobial is used to describe reduction in the number of viable pathanogenic or nuisance causing (e.g., odor causing, biological or physical degradation causing) microorganisms. The term non-fugitive is used to describe the nature of the acrylic antimicrobial component, which, barring exposure of the acrylic polymer itself to severe conditions of hydrolysis or decomposition, cannot be eliminated from the fiber.

These non-fugitive antimicrobial properties of this invention are ideal for reduction of disease causing microorganisms, protection against biological degradation, and are useful for odor reduction and mildew resistance, etc.

Acrylonitrile polymers, fibers and fabrics with antimicrobial properties would be useful as antimicrobial air and water filters for isolation purposes, solution stabilizers and membranes for purification and concentration purposes, medical devices for disease prevention in bandages, wound dressings, wipes, tampons, sponges, gowns, drainage tubes, catheters, sutures, etc., hygiene products for odor reduction in diapers, sanitary napkins, socks, etc., industrial products for mildew resistant paints, antimicrobial packaging materials for increased fruit and vegetable shelf life and for many other uses where microorganisms are encountered.

Additives may also be used with this invention to impart additional antimicrobial or other hygienic, biological, or medical protection to acrylic polymers, fibers or fabrics in end uses where additional reduction in the number of viable pathanogenic or nuisance causing microorganisms or elimination or deactivation of metabolic byproducts is desired.

Polymer Preparation Method:

One liter of demineralized water was added to a clean two liter water jacketed aluminum vessel. The water was blanketed with nitrogen gas and agitated between 50 and 150 revolutions per minute. The reaction temperature was set between 50° C. and 60° C. with heated water through the reaction vessel jacket. Individual monomers were weighed out in the desired amounts so the sum total of their weights was 400 grams. If used, the amine monomer was added to the reaction vessel first, and then the pH was adjusted with 10% sulfuric acid to 3.0±0.5. The remaining monomers were carefully added to the reaction vessel. The pH was checked again and adjusted if necessary. The temperature was checked and allowed to come back into limits before addition of the initiating agents. In the meantime, one of the following polymerization initiator solutions was prepared:

(1a) 8 grams of 77 ppm ferrous ammonium sulfate solution 20 grams of 11.5% hydrogen peroxide solution 30 grams of 7% 1-thioglycerol solution (1b) 8 grams of 77 ppm ferrous ammonium sulfate solution 20 grams of 11.5% hydrogen peroxide solution 30 grams of 7% thiourea solution (2) 8 grams of 77 ppm ferrous ammonium sulfate solution 30 grams of 20% sodium bisulfite solution 20 grams of 4.5% potassium persulfate solution (3) 5 grams of 2.2'-azobis (2-amidinopropane) hydrochloride 45 grams of demineralized water The initiator solution was then added to the reaction vessel, and the insuing reaction was watched closely. The agitator speed was slowly increased as the slurry began to thicken. Room temperature demineralized water was slowly added as the temperature began to rise. The reaction was run from the point of initiation for 60 minutes. If the slurry became too thick or the reaction temperature went too high, a small amount of slurry was drawn out and more room temperature demineralized water was slowly added.

At the end of the reaction time one of the following polymer quench solutions was added to the reaction vessel:

(1) 10 grams of 8% ethylenediaminetetraacetic acid solution 15 grams of 20% sodium bisulfite solution (2) 10 grams of 8% ethylenediaminetetraacetic acid solution (3) Cold water to reduce reaction temperature below 45° C.

After the appropriate quench solution was added, the polymer slurry was stirred for 15 minutes. The slurry was drawn out of the reaction vessel by vacuum aspiration and filtered on a Buckner funnel. The polymer was then removed from the filter funnel, reslurried in one liter of 80° C. demineralized water, stirred for 10 minutes, and filtered. The reslurry filtration step was repeated twice. The polymer was then slurried in reagent grade acetone, stirred 10 minutes, and filtered on a Buckner funnel. The washed polymer was then wrapped in cheese cloth, placed in a stainless steel pan and dried 16 to 24 hours in an air draft oven at 65° C.

Fiber Preparation

Fibers were prepared by standard acrylic dry spinning techniques. The polymer was dissolved in dimethylformamide up to a 23 to 33% solids level, heated to between 90° and 110° C., filtered, then heated to 110° to 150° C. and extruded through a 1400 hole spinneret at a spinning speed of 270 ypm. Nitrogen aspiration gas carried the solvent away as the individual filaments were formed. The fibers collected at the exit of the spinning cell had an as-spun denier per filament of 9.0. Residual solvent was extracted from the spun fiber in 90° to 100° C. water as the fiber was drawn either 4.5x or 6.0x to yield drawn denier per filaments of 2.0 and 1.5 respectively. Standard textile fiber finish was applied using a roll applicator to reduce interfiber friction and provide lubricity during subsequent textile processing. The finish applied contained a cationic antistat rather than an anionic antistat, since the anionic antistat would react with the protonated amine. The drawn fiber was then mechanically crimped and collected at the exit end of a draw-extration machine. The mechanically crimped yarn was then dried in a dryer between 90° and 120° C. to yield final denier per filament of 3.0 and 2.2 respectively.

Antimicrobial Activity Measurement Procedures:

The non-fugitive antimicrobial activity of polymers, fibers and fabrics were evaluated by the Shake Flask Test Procedure and the Parallel Streak Method.

A. Shake Flask Test

In the Shake Flask Test procedure, 70 ml of sterile pH 7.2 potassium hydrogen phosphate buffer solution was added to sterile 250 ml Erlenmeyer flasks. Each flask was then inoculated with 5 ml of a bacterial inoculum to yield $10^4$ colony forming units/ml solutions. The flasks were shaken well and time zero counts were made by removing 1 ml aliquots from each flask and making 1:10 and 1:100 dilutions in phosphate buffer. Duplicate pour plates of the 1:100 dilution in tryptone glucose extract agar were prepared, incubated at 37° C. for 18 to 24 hours and counted. One gram of test polymer or fiber was aseptically added to each flask. One extra flask was prepared containing the bacterial inoculum but no test solution to insure that the bacterial culture was viable in the test solution. The flasks were placed on a wrist action shaker and shaken for one to two hours. The one to two hour contact time counts were made by removing 1 ml aliquots from each flask and making 1:10 and 1:100 dilutions in phosphate buffer. Duplicate pour plates of both dilutions were prepared in tryptone glucose extract agar, incubated at 37° C. for 18 to 24 hours and the dilutions containing 30 to 300 counts were counted. The zero time counts and the one hour contact time counts were then corrected for their respective dilution factors, and 100 times the difference between the initial and final counts divided by the initial counts was the test item percent reduction. The shake flask procedure provided results on the relative bioactivities of various polymers, fibers and fabrics against a wide range of microorganisms. Results are given in Tables II-VI and VIII. The Shake Flask Test procedure is outlined in Malek, J.R. and Speier, J.L., *The Journal of Coated Fabrics*, Vol. 12, July, 1982, pp. 38–45.

B. Parallel Streak Method

To confirm the non-fugitivity of the antimicrobial component, the Parallel Streak Method was employed. Sterilized agar growth medium was prepared and 15 ml poured into each 100 mm diameter flat bottom petri dish. The agar was then allowed to firmly gel. A 1 ml sample of the desired test organism broth culture was transferred into 9 ml of sterile demineralized water and mixed by stirring with a 4 mm inoculating loop. One loopful of the diluted inoculum was transferred to a sterile agar plate by making five 7.5 cm long parallel streaks 1 cm apart in the center of the plate without refilling the loope, taking care not to break the agar surface. An oblong shaped test specimen was gently pressed transversely across the five inoculation streaks to insure intimate contact with the agar surface. The sample was then incubated for 18 to 24 hours at 37° C. The incubated plates were examined for interruption of growth along the streaks of inoculum underneath the sample and for a clear zone beyond the sample edge. The average width of the zone of inhibition around the test specimen was estimated with a ruler graduated in millimeters. Results are given in Table VII. This method is described in more detail in AATCC Test Method 147-1977.

TABLE I
AMINE CONTAINING ACRYLIC MONOMERS AND INITIATING AGENTS

| | M.W. g/mole |
|---|---|
| Monomers | |
| Dimethylaminoethylmethacrylate (DMAM) | 157 |
| Diethylaminoethylmethacrylate (DEAM or DEAEM) | 185 |
| Tertiarybutylaminoethylmethacrylate (TBAM) | 185 |
| Dimethylaminoneopentylacrylate (DMANPA) | 174 |
| 2-methyl-5-vinyl pyridine (MVP) | 119 |
| Dimethylaminopropylmethacryloamide (DMAPMA) | 170 |
| End Groups | |
| Thiourea | 76 |
| 2-amidinopropane hydrochloride | 121 |

EXAMPLE 1

Polymer samples were prepared according to the method described above. Acrylonitrile (AN) and methylacrylate (MA) monomers were copolymerized with various protonated amine containing monomers. These polymers were then challenged against Klebsiella pneumoniae in the Shake Flask Test. Results from these experiments are given in Table II. This example shows that the copolymerization of protonated amine containing monomers in acrylic polymers imparts antimicrobial activity.

TABLE II

| Item | Polymerization Initiator | Percent Monomer by Weight | | | | Shake Flask % Reduction (Klebsiella) | Quench System |
|---|---|---|---|---|---|---|---|
| | | AN | MA | Amine | (Name) | | |
| 1 | 2 | 94 | 6 | 0 | — | 40.0 | 2 |
| 2 | 2 | 90 | 6 | 4 | (DMAM) | 96.9 | 2 |
| 3 | 2 | 90 | 6 | 4 | (DEAM) | 99.7 | 2 |
| 4 | 2 | 90 | 6 | 4 | (TBAM) | 99.9 | 2 |
| 5 | 2 | 90 | 6 | 4 | (DMANPA) | 95.0 | 2 |
| 6 | 2 | 90 | 6 | 4 | (MVP) | 74.3 | 2 |
| 7 | 2 | 90 | 6 | 4 | (DMAPMA) | 96.2 | 2 |

EXAMPLE 2

To determine the effects of protonated amine containing end groups on polymer biactivity, a range of polymerization initiators were tested. Polymer samples were prepared according to the method described and challenged against Klebsiella pneumoniae in the Shake Flask Test. Results from these experiments, given in Table III, show that protonated amine containing end groups impart bioactivity to acrylic polymers.

TABLE III

| Item | Polymerization Initiator | Percent Monomer by Weight | | Shake Flask % Reduction (Klebsiella) | Quench Mixture | End* Group |
|---|---|---|---|---|---|---|
| | | AN | MA | | | |
| 8 | 1a | 94 | 6 | 36.4 | 1 | thioglycerol |
| 9 | 1b | 94 | 6 | 96.1 | 1 | thiourea |
| 10 | 2 | 94 | 6 | 40.0 | 2 | sulfonate |
| 11 | 3 | 94 | 6 | 99.8 | 3 | 2-amidinopropane |

*Thiourea and 2-amidino-propane end groups contain protonated amines. Thioglycerol and sulfonate end groups do not contain protonated amines.

EXAMPLE 3

To determine the minimum copolymerized protonated amine level required to produce a bioactive polymer, a series of polymers were prepared according to the method described above and then challenged against Klebsiella pneumoniae in the Shake Flask Test. Results from these experiments are given in Table IV.

TABLE IV

| Item | Polymerization Initiator | Percent Monomer by Weight | | | Shake Flask % Reduction (Klebsiella) | Quench Mixture |
|---|---|---|---|---|---|---|
| | | AN | MA | DEAM | | |
| 12 | 1a | 94 | 6 | 0 | 36.4 | 1 |
| 13 | 1a | 93.8 | 6 | 0.2 | 77.4 | 1 |
| 14 | 1a | 93.5 | 6 | 0.5 | 83.1 | 1 |
| 15 | 1a | 93 | 6 | 1 | 66.2 | 1 |
| 16 | 1a | 92 | 6 | 2 | 98.7 | 1 |
| 17 | 1a | 90 | 6 | 4 | 95.3 | 1 |

EXAMPLES 4–7

Examples 4, 5, 6, 7 include Items 18 and 19. As can be seen from Table V, Item 18 does not include any protonated amine, whereas Item 19 contains a protonated amine.

EXAMPLE 4

Polymers were prepared in a continuous overflow reaction and then spun into fibers according to the method described above. The bioactivity of the polymer and the fiber were determined in the Shake Flask Test against Klebsiella pneumoniae. Results of these experiments are given in Table V. These results demonstrate that bioactive polymer properties are retained when transformed into fiber.

TABLE V

| Item | Polymerization Initiator | Percent Monomer by Weight | | | Shake Flask % Reduction (Klebsiella) | | Quench Mixture |
| --- | --- | --- | --- | --- | --- | --- | --- |
| | | AN | MA | DEAM | Polymer | Fiber | |
| 18 | 2 | 94 | 6 | 0 | 2.3 | 3.4 | 2 |
| 19 | 1a | 90.7 | 6 | 3.3 | 98.8 | 99.9 | 1 |

EXAMPLE 5

Fiber samples were prepared according to the method described above and were challenged against a wide range of microorganisms in the Shake Flask Test. Results of these experiments are given in Table VI. These results demonstrate that fibers made from protonated amine containing acrylic polymers have a high level of bioactivity against a wide range of microorganisms.

TABLE VI

| | Shake Flask % Reduction | |
| --- | --- | --- |
| | Item 18 | Item 19 |
| Microorganism | | |
| A. niger (mold) | 19.7 | 62.5 |
| S. cerevisiae (yeast) | 33.1 | 74.4 |
| Cladosporium sp. (mildew) | 20.1 | 60.7 |
| Bacterial Inoculum | | |
| K. pneumoniae (Klebsiella) | 14.5 | 99.9 |
| E. coli | 8.2 | 99.9 |
| E. agglomerans | 32.0 | 99.9 |
| S. aureus | 23.1 | 99.9 |
| S. epidermidis | 25.1 | 99.9 |
| B. subtilis | 49.4 | 85.3 |
| P. aeruginosa | 54.0 | 99.0 |

EXAMPLE 6

Fiber samples were prepared according to the method described above and challenged against Klebsiella pneumoniae in the Parallel Streak Method, to confirm the nonfugitivity of amine containing acrylic fibers. Results from these experiments are given in Table VII.

TABLE VII

| | PARALLEL STREAK METHOD | |
| --- | --- | --- |
| | Growth Inhibition (Klebsiella) | |
| Item | Below Sample | Zone Around Sample (mm) |
| 18 | None | 0 |
| 19 | Complete | 0 |

EXAMPLE 7

Fiber samples prepared by the method described above were fabricated into nonwoven products and challenged against Klebsiella in the Shake Flask Test. Results from these experiments are given in Table VIII. These results demonstrate that the high level non-fugitive bioactivity found in protonated amine containing acrylic fibers is maintained in nonwoven fabrics.

TABLE VIII

| | Shake Flask % Reduction (Klebsiella) | |
| --- | --- | --- |
| Fabric | Item 18 | Item 19 |
| Hydraulically Needled | 38.5 | 99.9 |
| Thermally Bonded (25% polyester binder) | 44.3 | 99.9 |

I claim:

1. A method for imparting non-fugitive antimicrobial activity, effective in reducing viable microorganisms, exhibiting a shake flask percent reduction of Klebsiella of 70 to 100% to an article of manufacture comprising the steps of forming said article of manufacture from a polymeric acrylonitrile composition of:
   a. at least 85% by weight acrylonitrile.
   b. up to about 13% by weight of a neutral ethylenically unsaturated monomer, and
   c. from about 0.1 to 10% by weight of a protonated amine containing compound
where said antimicrobial activity is inherent in the acrylonitrile composition.

2. The method of claim 1 wherein the protonated amine containing compound is a protonated amine containing comonomer.

3. The method of claim 2 wherein the protonated amine containing comonomer is an acrylic monomer selected from the group consisting of Dimethylaminoethylmethacrylate (DMAM), Diethylaminoethylmethacrylate (DEAEM), Tertiarybutylaminoethylmethacrylate (TBAM), Dimethylaminoneopentyl acrylate (DMANPA), 2-methyl-5-vinyl pyridine (MVP), and Dimethylaminopropylmethacryloamide (DMAPMA).

4. The method of claim 2 or 3 wherein the microorganisms are gram-positive or gram-negative bacteria.

5. The method of claim 2 or 3 wherein the microorganisms are fungi.

6. The method of claim 2 or 3 wherein the microorganisms are yeasts.

7. The method of claim 2 or 3 wherein the microorganisms are spore-forming bacteria.

8. The method of claim 2 or 3 wherein the microorganisms are mold.

9. The method of claim 2 or 3 wherein the microorganisms are staphylococcus.

10. The method of claim 2 or 3 wherein the microorganisms are pseudomonas.

11. The method of claim 2 or 3 wherein the microorganisms are streptococcus.

12. The method of claim 2 or 3 wherein the microorganisms are bacillus.

13. The method of claim 2 or 3 wherein the article is a filter that would come in contact with the microorganisms.

14. The method of claim 2 or 3 wherein the article is a medical device that would come in contact with biological fluids.

15. The method of claim 2 or 3 wherein the article is a container for packaging food.

16. The method of claim 2 or 3 wherein the shake flask percentage reduction of Klebsiella is 99.9–100%.

17. The method of claim 2 or 3 wherein the acrylonitrile composition is a fiber, having a finish containing cationic antistat applied thereto.

18. The method of claim 1 wherein the protonated amine containing compound is a protonated amine containing polymer end group.

19. A method for imparting non-fugitive antimicrobial activity, effective in reducing viable microorganisms, exhibiting a shake flask percent reduction of Klebsiella of 70 to 100% to an article of manufacture comprising the steps of forming said article of manufacture from a polymeric acrylonitrile composition of:
 a. at least 85% by weight acrylonitrile,
 b. up to about 14% by weight of a neutral ethylenically unsaturated monomer, and
 c. from about 0.1 to 2.0% by weight of a protonated amine containing amidino group, connected to the polymer backbone selected from the group consisting of Thiourea and 2-amidinopropane hydrochloride.

20. A method of reducing viable microorganisms associated with a mammal which comprises contacting the skin or other parts of the mammal with an article of manufacture formed from an acrylonitrile composition of:
 (a) at least 85% by weight acrylonitrile
 (b) up to about 13% by weight of a neutral ethylenically unsaturated monomer, and
 (c) from about 0.1 to 10% by weight of a protonated amine containing compound.

21. The method of claim 20 wherein the article of manufacture is a tube.

22. The method of claim 20 wherein the article of manufacture is a fabric.

23. The method of claim 20 wherein the article of manufacture is a suture.

* * * * *